United States Patent [19]

Iacobucci et al.

[11] Patent Number: 6,004,913
[45] Date of Patent: *Dec. 21, 1999

[54] HIGH DI(ALKYL FATTY ESTER) QUATERNARY AMMONIUM COMPOUND IN ESTERAMINE FROM TRIETHANOLAMINE

[75] Inventors: Paul Albert Iacobucci, Patterson, N.Y.; Ralph Franklin, Danbury, Conn.; Phuong-Nga Trinh, Dobbs Ferry, N.Y.

[73] Assignee: Akzo Nobel N.V., Arnhem, Netherlands

[ * ] Notice: This patent is subject to a terminal disclaimer.

[21] Appl. No.: 08/984,968

[22] Filed: Dec. 4, 1997

Related U.S. Application Data

[62] Division of application No. 08/643,218, May 3, 1996, Pat. No. 5,916,863.

[51] Int. Cl.[6] ............ A61K 7/045; A61K 7/50; C11D 3/00; D06M 3/00
[52] U.S. Cl. ............ 510/123; 510/138; 510/329; 510/330
[58] Field of Search .................. 510/329, 330, 510/123, 138

[56] References Cited

U.S. PATENT DOCUMENTS

| | | | |
|---|---|---|---|
| 4,339,391 | 7/1982 | Hoffmann et al. | 260/401 |
| 4,429,859 | 2/1984 | Steiner et al. | 252/8.8 |
| 4,456,554 | 6/1984 | Walz et al. | 260/403 |
| 4,767,547 | 8/1988 | Straathof et al. | 252/8.8 |
| 4,789,491 | 12/1988 | Chang et al. | 252/8.75 |
| 4,830,771 | 5/1989 | Ruback et al. | 252/8.8 |
| 4,897,492 | 1/1990 | Bailey, III et al. | 548/352 |
| 4,963,274 | 10/1990 | Ruback et al. | 252/8.75 |
| 5,023,003 | 6/1991 | Yamamura et al. | 252/8.8 |
| 5,066,414 | 11/1991 | Chang | 252/8.8 |
| 5,296,622 | 3/1994 | Uphues et al. | 554/103 |
| 5,376,287 | 12/1994 | Borcher et al. | 252/8.8 |
| 5,399,272 | 3/1995 | Swartley et al. | 252/8.8 |
| 5,476,599 | 12/1995 | Rusche et al. | 252/88 |
| 5,637,743 | 6/1997 | Contet et al. | 554/52 |
| 5,916,863 | 6/1999 | Iacobucci et al. | 510/329 |

FOREIGN PATENT DOCUMENTS

| | | | |
|---|---|---|---|
| 1 163 275 | 3/1984 | Canada | 260/461.7 |
| 0 021 431 | 1/1981 | European Pat. Off. | C07C 101/18 |
| 0 413 249 | 2/1991 | European Pat. Off. | C11D 1/645 |
| 0 483 195 B1 | 5/1992 | European Pat. Off. | C07C 219/06 |
| 0 550 361 A1 | 7/1993 | European Pat. Off. | C07C 219/06 |
| 1 593 921 | 7/1970 | France . | |
| 43 08 792 | 4/1994 | Germany | C07C 219/06 |
| 42 42 480 | 6/1994 | Germany | D06M 13/463 |
| 42 43 701 | 6/1994 | Germany | D06M 13/463 |
| 2 160 421 | 12/1985 | United Kingdom | A61K 7/075 |
| 91-01295 | 2/1991 | WIPO . | |
| WO 91/01295 | 2/1991 | WIPO | C07C 219/06 |
| WO 93/21291 | 10/1993 | WIPO | C11D 1/62 |
| 94-20597 | 9/1994 | WIPO . | |
| WO 94/20597 | 9/1994 | WIPO | C11D 3/00 |
| WO 94/21596 | 9/1994 | WIPO | C07C 219/06 |

OTHER PUBLICATIONS

Abstract No. 91–058100/08 for WO 9101–295–A, dated Feb. 7, 1991.
Abstract No. DE–926740 for EP 413–249–A, dated Feb. 20, 1991.
English translation of French Patent No. 1 593 921, published Jul. 10, 1970, pp. 1–8 Process for treatment of textile products.
Abstract No.86–001611/01 for GB 2160–421–A, dated Oct. 24, 1985.
Derwent Abstract No. 93–005143/01 for JP 04333667–A, dated Nov. 20, 1992.
Derwent Abstract No. 93–165029/20 for JP 05098571–A, dated Apr. 20, 1993.
Derwent Abstract No. 04220 D/04 for EP 21–431, dated Jan. 7, 1981.

*Primary Examiner*—Mukund J. Shah
*Assistant Examiner*—Tamthom N. Truong
*Attorney, Agent, or Firm*—Ralph J. Mancini

[57] ABSTRACT

The present invention generally relates to a textile softening composition which comprises, as the softening agent, a quaternary ammonium salt which comprises a mixture of mono-, di-, and tri-ester components, wherein the amount of diester quaternary is greater than about 55% by weight, and the amount of triester quaternary is less than about 25% by weight based on the total amount of quaternary ammonium salt. The invention also relates to a process for preparing said softening agent.

23 Claims, No Drawings

HIGH DI(ALKYL FATTY ESTER) QUATERNARY AMMONIUM COMPOUND IN ESTERAMINE FROM TRIETHANOLAMINE

This is a divisional of application Ser. No. 08/643,218 filed May 3, 1996. Now U.S. Pat. No. 5,916,863.

FIELD OF THE INVENTION

The present invention generally relates to an improved softening composition containing quaternary ammonium compounds having high diester and low triester content and to a process for preparing same.

BACKGROUND OF THE INVENTION

The present invention relates to a quaternized diester based softener composition containing high diester content and low triester content. Compositions of this type have demonstrated unexpectedly superior softening performance and stability compared to compositions of the prior art.

Fabric softening compositions suitable for providing fabric softening and static control benefits during laundering are well known in the art. Such compositions generally contain, as the softening component, a substantially water insoluble quaternary ammonium compounds having two long alkyl chains.

Further, the use of various quaternized ester amines as fabric softening agents is also known in the art. U.S. Pat. No. 4,339,391 to Hoffmann, et al. for example, discloses a series of quaternized ester-amines which have utility as fabric softeners.

U. S. Pat. No. 5,296, 622 discloses quaternized ester amines having fabric-softening and hydrophilicizing properties which are obtained by reaction of unsaturated fatty acids containing at least 40 mol-% trans-configured double bonds or esters thereof with alkanolamines and subsequent quaternization of the reaction products with alkylating agents.

WO/93/21291 to Henkel claims textile treatment agents cox softener, quaternary ammonium compounds with 1, 2 or 3 acyloxyalkyl groups bound to the nitrogen atom. The compounds allegedly have a low viscosity if all or some of the acyl groups are derived from unsaturated fatty acids with a least 30% in the cis form.

U.S. Pat. No. 5,023,003 to KAO discloses a softener composition which comprises at least one quaternary ammonium salt of the following formulae:

(I)

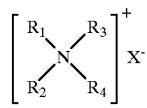

(II)

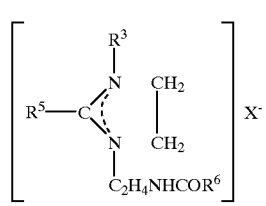

-continued

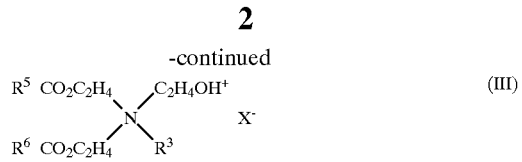

wherein $R^1$ and $R^2$ each represent a hydrocarbon radical having 12–22 carbon atoms, preferably 16–22 carbon atoms and one unsaturated bond; $R^3$ and $R^4$ represent a methyl, ethyl or

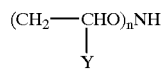

wherein n is a integer from 1 to 5, and Y is H or methyl; $R^5$ and $R^6$ each represent a hydrocarbon radical having 11–21 carbon atoms and one unsaturated bond; X represents halogen, $CH_3SO_4$, $C_2H_5SO_4$; wherein the stereoisomeric structure if the above said salt includes both the cis-isomer and the trans-isomer with the cis-isomer and the trans-isomer ratio being in the range of from 25/75 to 90/10.

U.S. Pat. No. 4,767,547 discloses fabric softening compositions containing an rapidly biodegradable quaternary ammonium softening agent of the formula:

(I)

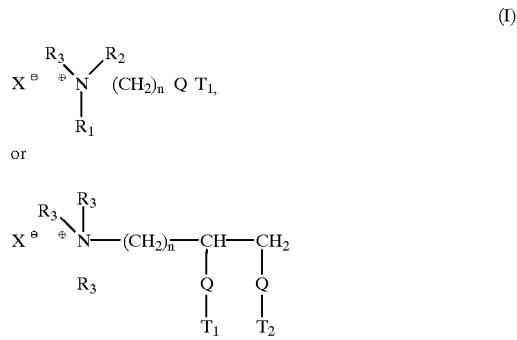

wherein:
Q is

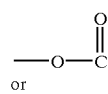

or

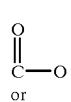

or

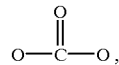

$R_1$, is $(CH_2)_n$-Q-$T_2$ or $T_3$;
$R_2$ is $(CH_2)_n$-Q-$T_4$ or $T_5$ or $R_3$;
$R_3$ is $C_1$–$C_4$ alkyl;
$T_1$, $T_2$, $T_3$, $T_4$, $T_5$ are (the same or different) $C_{12}$–$C_{22}$ alkyl or alkenyl;
n is an integer from 1 to 4; and $X^-$ is a softener-compatible anion, the composition having a pH, at 20° C., of from 2.5 to 4.2 upon dilution, in de-ionized water, to a concentration of 0.5% to 1% of said rapidly biodegradable quaternary ammonium compound.

WO 94/20597 to Procter & Gamble relates to softening compounds containing diester quaternary ammonium compounds wherein the fatty acyl groups have an Iodine Value of from greater than about 5 to less than about 100, a cis-trans isomer weight ratio of greater than about 30/70 when the Iodine Value is less than about 25, the level of unsaturation being less than about 65% by weight, wherein said compounds are capable of forming concentrated aqueous compositions with concentrations greater than about 13% by weight at an Iodine Value of greater than about 10 without viscosity modifiers other than normal polar organic solvents present in the raw material of the compound or added electrolyte.

EP 0 550 361 to Stepan discloses cationic fabric treating compositions which comprises quaternary ammonium compounds which are the reaction product of a long chain fatty acid and a tertiary amine wherein the ratio of fatty acid to amine is between 1.85 and 1.4.

WO 91/01295 to Henkel discloses quaternary ammonium compounds useful as textile treatment agents which are prepared by reaction of fatty acids with alkanolamine and thereafter alkylating same to give the quaternary compounds. The esterification reaction is carried out in the presence of an acid catalyst such as hypophosphorous acid. The final product allegedly comprises mono-, di- and triester components in a ratio of 10:62:28%. There is no disclosure, however, of a process for the preparation of a final product having high diester content, i.e., greater than about 55% by weight, and low triester content, i.e., lower than about 20% by weight.

Finally, WO 94/14935 to Henkel discloses concentrated textile softener dispersions containing quaternary ammonium compounds derived from triethanolamine and containing one, two or three fatty acyloxyethyl groups. When the proportion of compounds having two fatty acyloxyethyl groups is larger than 50% by moles, these compounds allegedly have a particularly low viscosity. However, no process to achieve this level of diester was disclosed in this document, and there is no indication of the triester content of the final product.

Therefore, it is clear that the prior art discussed hereinabove does not contemplate or suggest the quaternized diester based softener composition containing high diester content and low triester content. A process for the preparation of such products is also not contemplated.

Accordingly, it is an object of the present invention to provide quaternized diester product having high diester content and low triester content. It is a further object of the present invention to provide a textile softening composition which comprises as a major ingredient the quaternary diester compound of the present invention. Another object of the present invention is to provide a textile softening composition which is non-yellowing and has improved softening performance and desirable textile softening properties such as improved softener biodegradability, viscosity, water absorbency, stability and the like. These and other objects are readily apparent from the following disclosure.

SUMMARY OF THE INVENTION

The present invention generally relates to a textile softening composition which comprises, as the softening agent, a quaternary ammonium salt which comprises a mixture of mono-, di- and tri-ester components, wherein the amount of diester quaternary is greater than about 55% by weight, and the amount of triester quaternary is less than about 20% by weight based on the total amount of quaternary ammonium salt. The invention also relates to a method for preparing said softening agent.

DETAILED DESCRIPTION OF THE INVENTION

The present invention generally relates to a textile softening composition which comprises a quaternary ammo-nium based softening agent which is high in diester and low in triester content and to a process for the preparation of same. Quaternary ammonium compounds having particularly good performance and stability profiles are obtained by reaction of $C_{12}$–$C_{22}$ fatty acids or the hydrogenation products thereof, or a mixture of such acids, with an alkanolamine in the presence of an acid catalyst, wherein the ratio of fatty acid to alkanolamine is from about 1.60–1.80. The resultant esteramine reaction products are subsequently quaternized to obtain the quaternary ammonium salts of the present invention.

Preferably, the fatty acid is a $C_{16}$–$C_{22}$ acid containing a degree of unsaturation such that the iodine value ("IV") is in the range of from about 20–90, more preferably, from about 40–60, and still more preferably, in a range of from about 45–55. Preferred fatty acids include but are not limited to oleic, palmitic, erucidic, eicosanic and mixtures thereof. Soy, tallow, palm, palm kernal, rape seed, lard, mixtures thereof and the like are typical sources for fatty acid which can be employed in the present invention. Partial hydrogenation can be employed, if required, to minimize the polyunsaturate levels in order to improve the stability of the final product. It is also preferred that the fatty acid(s) employed in the present process have a cis to trans isomer ratio of from about 80:20 to about 95:5. More preferably, the trans-isomer content of said fatty acid(s) is less than about 10%. An optimum trans-isomer content is between about 0.5–9.9%. The most preferred fatty acid is a mixture of tallow/distilled tallow having a cis:trans isomer ratio of greater than 9:1.

The alkanolamines employable in the present invention generally correspond to the formula:

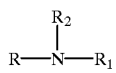

wherein R, $R_1$ and $R_2$ are independently selected from $C_2$–$C_4$ hydroxyalkyl groups. Preferred alkanolamines include but are not limited to triethanolamine, propanol diethanolamine, ethanol diisopropanolamine, triisopropanol amine and mixtures thereof. Triethanolamine is the most preferred alkanolamine.

The molar ratio of fatty acid to alkanol amine is generally in the range of from about 1.60–1.80, and more preferably, in the range of from about 1.65–1.75. Best results are usually obtained when the molar ratio is about 1.70.

The acid catalyst employable in the present process includes but is not limited to sulphonic acid, phosphorous acid, p-toluene sulphonic acid, methane sulphonic acid, oxalic acid, hypophosphorous acid or an acceptable Lewis acid. A preferred acid catalyst is hypophosphorous acid. Typically, 0.02–0.2% by weight, and more preferably 0.1 to 0.15% by weight of acid catalyst, based on the weight of fatty acid, in employed in the present process.

The esterification of fatty acids with alkanolamines is carried out at a temperature of from about 175°–210° C. until the reaction product has an acid value of below 5. Further, triester formation in the final product can be minimized by controlling the heat up rate for forming the esteramine mixture. Typically, a heat up rate of 0.8°–3° C./minute, preferably 1.25° to 3° C., from a temperature of about 70° C. to a temperature in a range of from between 170° C. to 210° C. is effective in minimizing triester formation. After the esterification, the crude product is reacted with alkylating agents in order to obtain the quaternary ammonium product. Preferred alkylating agents include $C_1$–$C_3$ straight or branched chain alkyl halides, phosphates or sulfates, $C_7$–$C_{10}$ aralkyl halides, phosphates or sulfates, and mixtures thereof. Examples of preferred alkylating agents include but are not limited to methyl chloride, benzyl chloride, diethyl sulfate, dimethyl carbonate, trimethyl phosphate, dimethyl sulfate or mixtures thereof. Choosing the type and amount of alkylating agent employed is well within the skill of one in the art. Typically, when dimethyl sulfate is the alkylating agent, 0.7 to 1.0 mol dimethyl sulfate per mole of ester is satisfactory in yielding the quaternized product The quaternization may be carried out in bulk or in solvent, at temperatures ranging from 60°–120° C. If a solvent is employed, then the starting materials and/or product must be soluble in the solvent to the extent necessary for the reaction. Solvents of this type are generally known in the art. Suitable examples include polar solvents such as, for example, lower alcohols, i.e., $C_1$–$C_6$ alcohols. Other solvents which can be employed include, but are not limited to mono-, di-, and tri-glycerides, fatty acid, glycol and mixtures thereof.

The resultant quaternary ammonium salt comprises a mixture mono - (I), di - (II) and tri-ester (III) components of the following formulae:

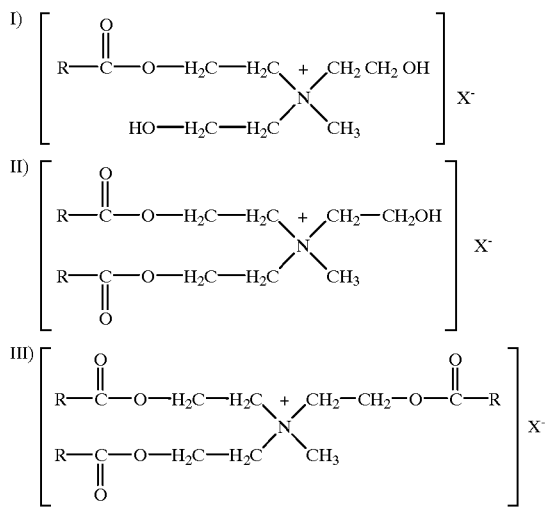

wherein R represents a hydrocarbon radical having 12–22 carbon atoms, preferably 16–22 carbon atoms, having a total IV in the range of 20–90, preferably, 40–60, and more preferably, 45–55, and )X⁻ represents a softener compatible anion including but not limited to halogen, $CH_3SO_4$ or $C_2H_5SO_4$. The reaction products may also contain minor amounts of methyl triethanolamine quaternary and other impurities. Further, the amount of diester in the final product is generally greater than about 55% by weight and the amount of triester is generally less than about 25%, preferably less than 20% by weight based on the total amount of quaternary ammonium salt product. Typical formulations contain 60–65 wt % diester and less than about 18 wt % triester, more preferably, less than about 15 wt % triester. Further, the ratio of cis to trans double bonds of the above salts is preferably in the range of from about 80:20 to about 95:5. In a most preferred embodiment, the amount of trans isomer is less than about 10%, and ideally in the range of from 5 to 9.5%.

There are several convenient methods for obtaining the desired cis:trans ratio of the quaternary ammonium salt product. The preferred method is to produce the quaternary ammonium salt from a cis-isomeric and trans-isomeric fatty acids after adjusting said acids to the desired ratio.

Another method is to produce the quaternary ammonium salt from the mixture after adjusting the ratio thereof by isomerizing a portion of the cis-isomeric fatty acid or ester thereof into the trans-isomer, in the presense of a metallic catalyst. Other methods are readily apparent to and well within the skill of one of ordinary skill in the art.

The textile softening composition of the present invention having high diester content and low triester content demonstrates superior performance compared to typical esteramine quaternary compounds, and the excellent color and odor stability allows the formulator greater latitude in preparing high quality softening products. The compositions can be aqueous liquids, preferably concentrated, containing from about 4–50%, preferably from about 10 to 45% and still more preferably from about 15–40% by weight of the quaternary ammonium compounds of the present invention. The compositions of the present invention can be further concentrated to particulate solids containing from about 50–95%, preferably 60–90% quaternary ammonium softening compound, if desired.

The liquid carrier employed in the compositions of the present invention is preferably water due to its availability, safety, environmental compatibility and low cost. The level of water in the liquid carrier is generally at least about 50%, more preferably, at least about 60% by weight of the carrier. The level of liquid carrier is less than about 70%, preferably, less than 60%. Mixtures of water and low molecular weight solvents, i.e., for example, lower alcohols such as ethanol, propanol, isopropanol, butanol and the like, and low molecular weight alcohols such as monohydric, dihydric, trihydric and higher polyhydric alcohols are also useful as the liquid carrier. The presence of organic solvents does not harm the storage stability, the viscosity, or the softening performance of the compositions of this invention. There is no need to remove such a solvent in making the compositions of this invention.

Water can be added to the particulate solid compositions to form either dilute or concentrated liquid textile softening compositions according to the invention. The solid particulate composition can also be directly added to the rinse bath in order to provide an adequate usage concentration, which is typically in the range of from about 10–1000 ppm, more preferably, in a range of from about 50–500 ppm.

The quaternary ammonium compounds according to the present invention can generally be prepared by reacting at least one $C_{12}$–$C_{22}$ fatty acid having a IV of from 20–90 with an alkanol amine in the presence of an acid catalyst. The ratio of acid to amine is preferably in the range of 1.6 to 1.8, and the reaction is carried out at a temperature of from about 175° C. to about 210° C. until the reaction product has an acid value of below about 5. A heat up rate of 0.8° C. to 3.0° C. per minute is employed in order to minimize triester formation. The esterification products are subsequently alkylated in order to obtain the quaternary ammonium product.

A standard rinse-cycle softening composition in accordance with the present invention can be prepared by preheating water to a temperature of from about 45°–60° C. in a suitable vessel and acidifying same to a pH of from about 2.7–3.2. The warmed quaternary ammonium salt is thereafter added to the acidified water with agitation while the temperature is maintained at 45° C. –60° C. Fragrance and other optional ingredients can then be solubilized into the softener dispersion, and the weight is thereafter adjusted with deionized water. Dispersions such as this are typically storage stable within a temperature range of from about 4° C. to about 50° C.

The quaternary ammonium salts of the present invention may also be utilized in products other than fabric softening compositions. These products may include hair care formulations, skin care formulations, and the like, for the softening, lubrication, emolliency and condition of said hair and/or skin when applied in effective amounts. These and other uses will be readily apparent to one of ordinary skill in the art.

Although the stability of the textile softening compositions of the present invention is such that stabilizing cosurfactants are not required, they may nevertheless be included along with a wide variety of other optional ingredients. A brief non-limiting description of some of the optional ingredients which may be employed in the textile softening compositions of the present invention is provided below.

I.) Viscosity/Dispersibility Aids

As previously mentioned, relatively concentrated compositions of the quaternary esters of the present invention can be prepared that are stable, without the addition of concentration aids. However, the compositions of the present invention may require organic and/or inorganic concentration aids to go to even higher concentrations and/or to meet higher stability standards depending on the other ingredients. These concentration aids which are typically viscosity modifiers may be needed, or preferred, for ensuring stability under extreme conditions when particular softener active levels in relation to IV are present.

Surfactant Concentration Aids

Surfactant concentration aids typically falls into four catagories:
(1) mono long chain alkyl cationic surfactants;
(2) nonionic surfactants;
(3) amine oxides; and
(4) fatty acids.

Mixtures of the aforementioned surfactant concentration aids can, of course, also be employed.

(1) Mono-Long Chain Alkyl Cationic Surfactants

Preferred mono-long chain alkyl or ester based water-soluble cationic surfactants generally fall within the scope of the following general formula:

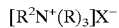

wherein the $R^2$ group is $C_8$–$C_{22}$ hydrocarbon group, preferably $C_{12}$–$C_{18}$ alkyl group or the corresponding ester linkage interrupted group with a short chain alkylene ($C_1$–$C_4$) group between the ester linkage and the N, and having a similar hydrocarbon group, e.g., a fatty acid ester of choline, preferably $C_{12}$–$C_{14}$ (coco) choline ester and/or C$_6$–$C_{18}$ tallow choline ester at from about 0.1% to about 20% by weight of the softener active. Each R is a $C_1$–$C_6$ unsubstituted or substituted alkyl (e.g., by hydroxy) or hydrogen, preferably methyl, and the counterion X- is a softener compatible anion such as, for example, chloride, bromide, methyl sulfate, etc.

The cationic surfactants, if present, are usually added to solid compositions at a level of from 0% to about 15%, preferably from about 3% to about 15%, more preferably from about 5% to about 15%. In liquid compositions they are usually employed at level of from 0% to about 15%, preferably from about 0.5% to about 10%. In general, the total amount single-long-chain cationic surfactant is added in an amount effective to obtain a stable composition.

The foregoing levels represent the amount of the single-long-chain-alkyl cationic surfactant which is added to the composition of the present invention. The ranges do not include the amount of monoester which is already present in the diester quaternary ammonium compound.

The long chain group $R^2$, of the single-long-chain-alkyl cationic surfactant generally contains an alkylene group having from about 10 to about 22 carbon atoms, preferably from about 12 to about 16 carbon atoms for solid compositions, and preferably from about 12 to about 18 carbon atoms for liquid compositions. This $R^2$ group can be attached to the cationic nitrogen atom through a group containing one, or more, ester, amide, ether, amine, etc., preferably ester, linking groups which can be desirable for increased hydrophilicity, biodegradability, etc. Such linking groups are preferably within about three carbon atoms of the nitrogen atom. Suitable biodegradable single-long-chain alkyl cationic surfactants containing an ester linkage in the long chain are described in U.S. Pat. No. 4,840,738 which is incorporated herein by reference. If the corresponding, non-quaternary amines are used, any acid (preferable a mineral or polycarboxylic acid) which is added to keep the ester groups stable will also keep the amine protonated in the compositions and preferably during the rinse so that the amine has a cationic group. The composition is buffered (pH from about 2 to about 5, preferably from about 2 to about 4) to maintain an appropriate, effective charge density in the aqueous liquid concentrate product and upon further dilution e.g., to form a less concentrated product and/or upon addition to the rinse cycle of a laundry process.

The main function of the water-soluble cationic surfactant is to lower the viscosity and/or increase the dispersibility of the diester softener and it is not, therefore, essential that the cationic surfactant itself have substantial softening properties, although this may be the case. Also, surfactants having only a single long alkyl chain, presumably because they have greater solubility in water, can protect the diester softener from interacting with anionic surfactants and/or detergent builders that are carried over into the rinse. Other cationic materials with ring structures such as alkyl imidazoline, imidazolimium, pyridine, and pyridinium salts having a single $C_{12}$–$C_{30}$ alkyl chain can also be used. Very low pH is required to stabilize, e.g., imidazoline ring structures. Some alkyl imidazolinium salts useful in the present invention have the general formula:

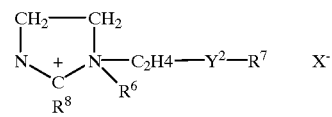

wherein $Y^2$ is —C(O)—O—, —O—(O)—C—, —C(O)—N($R^5$), or —N($R^5$)—C(O)—in which $R^5$ is hydrogen or a $C_1$–$C_4$ alkyl radical; $R^6$ is a $C_1$–$C_4$ alkyl radical; $R^7$ and $R^8$ are each independently selected from R and $R^2$ as defined hereinbefore for the single-long-chain cationic surfactant with only one being $R^2$. Some alkyl pyridinium salts useful in the present invention have the general formula:

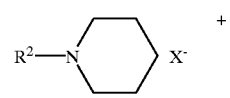

wherein $R^2$ and $X^-$ are as defined above. A typical material of this type is cetyl pyridinium chloride.

(2) Nonionic Surfactants — Alkoxylated Materials.

Nonionic surfactants suitable as viscosity/dispersibility modifiers include the addition products of ethylene and/or propylene oxide with fatty alcohols, fatty acids, fatty amines, etc. Any of the alkoxylated materials hereinafter described can be used as the nonionic surfactant. In general terms, the nonionics herein can be employed in solid compositions at a level of from about 5% to about 20%, preferably from about 8% to about 15%, and in liquid compositions at a level of from 0% to about 5%, preferably from about 0.1% to about 5%, more preferably from about 0.2% to about 3%.

Suitable water-soluble nonionic surfactants generally fall within the scope of the following general formula:

$$R^2-Y-(C_2H_4O)z-C_2H_4OH$$

wherein $R^2$ for both solid and liquid compositions is selected from the group consisting of primary, secondary and branched chain alkenyl hydrocarbyl groups; and primary, secondary and branched chain alkyl- and alkenyl-substituted phenolic hydrocarbyl groups; said hydrocarbyl groups having a hydrocarbyl chain length of from about 8 to about 20, preferably from about 10 to about 18 carbon atoms. More preferably the hydrocarbyl chain length for liquid compositions is from about 16 to about 18 carbon atoms and for solid compositions form about 10 to about 14 carbon atoms. In the general formula for the ethoxylated nonionic surfactants herein, Y is typically —O—, —C(O)—, —C(O)N(R)—, or —C(O)N(R)R—, wherein R, when present, has the meanings given hereinbefore, and/or R can be hydrogen, and z is at least about 8, preferably at least about 10–11. Performance, and usually stability of the softener composition decrease when fewer ethoxylate groups are present.

The nonionic surfactants herein are characterized by an HLB (hydrophilic-lipophilic balance) of from about 7 to about 20, preferably from about 8 to about 15. By defining $R^2$ and the number of ethoxylate groups, the HLB of the surfactant is, for the most part, determined. However, it is preferred that for concentrated liquid compositions, the nonionic surfactants contain relatively long chain $R^2$ groups and are relatively highly ethoxylated. While shorter alkyl chain surfactants having short ethoxylated groups may possess the requisite HLB, they are not as effective. Nonionic surfactants as the viscosity/dispersibility modifiers are preferred over the other modifiers disclosed herein for compositions with higher levels of perfume.

Nonionic surfactants employable in the present invention include but are not limited to the following examples. In the examples, the number of ethoxyl groups in the molecule (EO) is defined by an integer.

(i) Straight-Chain. Primary Alcohol Alkoxylates

The deca-, undeca-, dodeca-, tetradeca-, and pentadeca-ethoxylates of n-hexadecanol, and n-octadecanol having an HLB within the preferred range are useful as viscosity/dispersibility modifiers of the context of this invention. Preferred examples of ethoxylated primary alcohols useful herein as the viscosity/dispersibility modifiers of the compositions include but are not limited to n-$C_{18}$EO(10); and n-$C_{10}$EO (11). The ethoxylates of mixed natural or synthetic alcohols in the "tallow" chain length range are also useful herein. Specific examples of such materials include tallow alcohol-EO(11), tallow alcohol-EO(18), and tallow alcohol-EO(25).

(ii) Straight-Chain. Secondary Alcohol Alkoxylates

The deca-, undeca-, dodeca-, tetradeca-, pentadeca-, octadeca-, and nonadeca-ethoxylates of 3-hexadecanol, 2-octadecanol, 4-eicosanol, and 5-eicosanol having an HLB within the preferred range are useful viscosity/dispersibility modifiers in the context of the present invention. Examples of ethoxylated secondary alcohols useful herein as the viscosity/dispersibility modifiers of the compositions include but are not limited to: 2–$C_{16}$EO(11); 2–$C_{20}$EO(11); and 2–$C_{16}$EO(14).

(iii) Alkyl Phenol Alkoxylates

As is the case of the alcohol alkoxylates, the hexa- through octadeca-ethoxylates of alkylated phenols, particularly monohydric alkylphenols, having an HLB within the preferred range are useful as the viscosity/dispersibility modifiers. The hexa- through octadeca-ethoxylates of p-tridecylphenol, m-pentadecylphenol, and the like, are useful herein. Preferred examples of ethoxylated alkylphenols useful as the viscosity/dispersibility modifiers include but are not limited to: p-tridecylphenol EO(11) and p-pentadecylphenol EO(18).

It would be generally recognized by one of ordinary skill in the art that a phenylene group in the nonionic formula is the equivalent of an alkylene group containing from 2 to 4 carbon atoms. For present purposes, nonionic surfactants containing a phenylene group are considered to contain an equivalent number of carbon atoms calculated as the sum of the carbon atoms in the alkyl group plus about 3.3 carbon atoms for each phenylene group.

(iv) Olefinic Alkoxylates

The alkenyl alcohols, both primary and secondary, and alkenyl phenols corresponding to those disclosed hereinabove can be ethoxylated to an HLB within the range recited herein and used as the viscosity/dispersibility modifiers in the compositions of the present invention.

(v) Branched Chain Alkoxylates

Branched chain primary and secondary alcohols which are available from the well-known "OXO" process can be ethoxylated and employed as the viscosity/dispersibility modifiers in the present compositions.

The ethoxylated nonionic surfactants summarized hereinabove can be usefully employed in the present compositions either alone or in specific mixtures.

(3) Amine Oxides

Suitable amine oxides include but are not limited to those with one alkyl or hydroalkyl moiety of about 8 to about 28 carbon atoms, preferably from about 8 to about 16 carbon atoms, and two alkyl moieties selected from the group consisting of alkyl groups and hydroxyalkyl groups with about 1 to about 3 carbon atoms. Amine oxides, if employed, are generally present in solid compositions at a level of from 0% to about 15%, preferably from about 3% to about 15%; and in liquid compositions at a level of from 0% to about 5%, preferably from about 0.25% to about 2%. The total amount amine oxide is generally present in an amount effective to provide a stable composition.

Preferred examples of amine oxides employable in the present invention include but are not limited to dimethyloctylamine oxide, diethyldecylamine oxide, bis-(2-hydroxyethyl)dodecylamine oxide, dimethyl dodecylamine oxide, dipropyltetradecylamine oxide, methylethylhexadecylamine oxide, dimethyl-2-hydroxyoctadecylamine oxide, and coconut fatty alkyl demethylamine oxide.

(4) Fatty Acids

Suitable fatty acids include those containing from about 12 to about 25, preferably from about 13 to 22, more preferably from about 16 to about 20, total carbon atoms, with the fatty moiety containing from about 10 to about 22, preferably from about 10 to about 18, more preferably from about 10 to about 14 carbon atoms. The shorter moiety contains from about 1 to about 4, preferably from about 1 to about 2 carbon atoms. Fatty acids are typically present at approximately the levels outlined above for amine oxides. Fatty acids are preferred concentration aids for those compositions which require a concentration aid and contain perfume.

Electrolyte Concentration Aids

Inorganic viscosity control agents which can also act like or augment the effect of the surfactant concentration aids include water-soluble, ionizable salts. Such salts can also optionally be incorporated into the compositions of the present invention. A wide variety of ionizable salts can be used. Examples of suitable salts include but are not limited to the halides of the Group IA and IIA metals of the Periodic Table of Elements, e.g., calcium chloride, magnesium chloride, sodium chloride potassium bromide, and lithium chloride. The ionizable salts are particularly useful during the process of mixing the ingredients to make the compositions herein, and to obtain the desired viscosity. The amount of ionizable salts used depends on the amount of active ingredients used in the compositions. Typical levels of salts used to control the composition viscosity are from about 20 to about 20,000 parts per million (ppm), preferably from about 20 to about 11,000 ppm, by weight of the composition.

Alkylene polyammonium salts can be incorporated into the composition to give viscosity control in addition to or in place of the water-soluble, ionizable salts described above. Additionally, these agents can act as scavengers, forming ion pairs with anionic detergent carried over from the main wash to the rinse and may improve softening performance. These agents may stabilize the viscosity over a broader range of temperature, especially at low temperatures, compared to the inorganic electrolytes. Specific examples of alkylene polyammonium salts include but are not limited to 1-lysine monohydrochloride and 1,5-diammonium 2-methyl pentane dihydrochloride.

II) Stabilizers

Stabilizers may also be optionally employed in the compositions of the present invention. The term "stabilizer," as used herein, includes antioxidants and reductive agents. These agents are typically present at levels of from 0% to about 2%, preferably from about 0.01% to about 0.2%, more preferably from about 0.05% to about 0.1% for antioxidants and more preferably from about 0.01% to about 0.2% for reductive agents. Stabilizer use assures good odor stability under long term storage conditions. Further, use of antioxidants and reductive agent stabilizers is especially critical for unscented or low scent products.

Examples of antioxidants which can be employed in the compositions of the present invention include but are not limited to a mixture of ascorbic acid, ascorbic palmitate, propyl gallate, available from Eastman Chemical Products, Inc., under the trade names Tenox® PG and Tenox S-1; a mixture of BHT (butylated hydroxytoluene), BHA (butylated hydroxyanisole), propyl gallate, and citric acid, available from Eastman Chemical Products, Inc., under the trade name Tenox-6; butylated hydroxytoluene, available from UOP Process Division under the trade name Sustane® BHT; tertiary butylhydroquinone available from Eastman Chemical Products, Inc. under the mark Tenox® & TBHQ; natural tocopherols available from Eastman Chemical Products, Inc. under the mark Tenox® GT-1/GT-2; and butylated hydroxyanisole available from Eastman Chemical Products, Inc., as BHA; long chain esters ($C_8$–$C_{22}$) of gallic acid such as dodecyl gallate; Irganox® 1010; Irganox® 1035; Irganox® B 1171; Irganox® 1425; Irganox® 3114; Irganox® 3125; and mixtures thereof; preferably Irganox® 3125, Irganox® 1425, Irganox® 3114, and mixtures thereof; and more preferably Irganox® 3125 alone or in combination with citric acid and/or other chelators such as isopropyl citrate, Dequest®) 2010 available from Monsanto under the name 1-hydroxyethylidene-1, 1-diphosphonic acid (etidronic acid), Tiron®, available from Kodak with a chemical name of 4,5-dihydroxy-m-benzene-sulfonic acid/ sodium salt, and DTPA® (diethylenetriaminepentaacetic acid), available from Aldrich. The chemical names and CAS numbers for some of the above stabilizers are tabulated below.

| Antioxidant | CAS No. | Chemical Name used in Code of Federal Regulations |
|---|---|---|
| Irganox ® 1010 | 6683-19-8 | Tetrakis [methylene(3,5-di—tert-butyl-4 hydroxyhydrocinnamate)] methane |
| Irganox ® 1035 | 41484-35-9 | Thiodiethylene bis(3,5-di—tert-butyl-4-hydroxyhydrocinnamate |
| Irganox ® 1098 | 23128-74-7 | N,N'-hexamethylene bis(3,5-di—tert-butyl-4-hydroxy hydrocinnammamide |
| Irganox ® B 1171 | 31570-04-4 23128-74-7 | 1:1 Blend of Irganox ® 1098 and Irgafos ® 168 |
| Irganox ® 1425 | 65140-91-2 | Calcium bis[monoethyl(3,5-di—tert-butyl-4-hydroxybenzyl)phosphonate] |
| Irganox ® 3114 | 27676-62-6 | 1,3,5-Tris (3,5-di—ter-butyl-4-hydroxybenzyl)-s-triazine-2,4,6-(1H, 3H, 5H)trione |
| Irganox ® 3125 | 34137-09-2 | 3,5-Di—tert-butyl-4-hydroxy-hydrocinnamic acid triester with 1,3,5-tris(2-hydroxyethyl)-S-triazine-2,4,6-3H, 5H)trione |
| (1H, Irgafos ® 168 | 31570-04-4 | Tris(2,4-di—tert-butyl-phenyl) phosphite |

Examples of reductive agents include but are not limited to sodium borohydride, sodium bisulfide, hypophosphorous acid, and mixtures thereof. The stability of the compounds and compositions herein can be improved by use of stabilizers, but in addition, the preparation of compounds used herein and the source of hydrophobic groups can be important. Surprisingly, some highly desirable, readily available sources of hydrophobic groups such as fatty acids from, e.g., tallow, possess odors that remain with the compound despite the chemical and mechanical processing steps which convert the raw tallow to finished product. Such sources must be deodorized, e.g., by absorption, distillation, stripping, etc., as is well known in the art. In addition, contact of the resulting fatty acyl groups to oxygen and/or bacteria must be minimized by adding antioxidants, antibacterial agents, etc.

Additional Optional Ingredients

Soil Release Agent

The composition of the present invention may optionally contain from 0.1% to 10%, preferably from 0.2% to 5%, of a soil release agent. Preferably, the soil release agent is a polymeric soil release agent such as one which contains copolymeric blocks of terephthalate and polyethylene oxide or polypropylene oxide, cationic guar gums, and the like. U.S. Pat. No. 4,956,447, which is incorporated herein by reference, discloses some preferred soil release agents comprising cationic functionalities.

A preferred soil release agent is copolymer having blocks of terephthalate and polyethylene oxide which are comprised of repeating units of ethylene terephthalate and polyethylene oxide terephthalate at a molar ratio of ethylene terephthalate units to polyethylene oxide terephthalate units of from about 25:75 to about 35:65, said polyethylene oxide terephthalate containing polyethylene oxide blocks having molecular weights of from about 300 to about 2,000. The molecular weight of this polymeric soil release agent is in the range of from about 5,000 to about 55,000.

Another preferred polymeric soil release agent is a crystallizable polyester with repeat units of ethylene terephthalate units containing from about 10% to about 15% by weight of ethylene terephthalate units together with from about 10% to about 50% by weight of polyoxyethylene glycol of average molucular weight of from about 300 to about 6,000, wherein the molar ratio of ethylene terephthalate units to polyoxyethylene terephthalate units in the crystallizable polymeric compound is between 2:1 and 6:1. Examples of this polymer include but are not limited to Zelcon® 4780 available from DuPont and Milease® T available from ICI. Highly preferred soil release agents are polymers of the generic formula (I):

units, it is usually desirable to minimize the degree of partial substitution with moieties other than 1,4-phenylene for best soil release activity. Preferably, the $R^1$ moieties consist entirely of (i.e., comprise 100%) 1,4-phenylene moieties, i.e., each $R^1$ moiety is 1,4-pheneylene.

For the $R^2$ moieties, suitable ethylene or substituted ethylene moieties include but are not limited to ethylene, 1,2-propylene, 1,2-butylene, 1,2-hexylene, 3-methoxy-1,2-propylene and mixtures thereof. Preferably, the $R^2$ moieties are essentially ethylene moieties, 1,2-propylene moieties or mixtures thereof. Inclusion of a greater percentage of ethylene moieties tends to improve the soil release activity of compounds. Inclusion of a greater percentage of 1,2-propylene moieties tends to improve the water solubility of the compounds.

The use of 1,2-propylene moieties or a simular branched equivalent is desirable for incorporation of any substantial part of the soil release component in the liquid fabric softener compositions. Preferably, from about 75% to about 100%, more preferably from about 90% to about 100%, of (I)

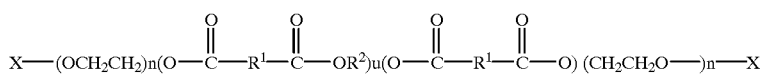

in which X can be any suitable capping group, wherein each X is selected from the group consisting of H, and alkyl or acyl groups containing from about 1 to about 4 carbon atoms, wherein methyl is preferred. n is selected for water solubility and is generally from about 6 to about 113, preferably from about 20 to about 50. u is critical to liquid formulations having a relatively high ionic strength. The amount of material wherein u is greater than 10 should be minimized, while there should be at least 20%, preferably at least 40%, of material in which u ranges from about 3 to about 5.

The $R^1$ moieties are essentially 1,4-phenylene moieties. As used herein, the term "the $R^1$ moieties are essentially 1,4-phenylene moieties" refers to compounds where the $R^1$ moieties consist entirely of 1,4-phenylene moieties, or are partially substituted with other arylene or alkarylene moieties, alkylene moieties, alkenylene moieties, or mixtures thereof. Arylene and alkarylene moieties which can be partially substituted for 1,4-phenylene include 1,3-phenylene, 1,2-phenylene, 1,8-naphtylene, 1,4-naphthylene, 2,2-biphenylene, 4,4-biphenylene and mixtures thereof. Alkylene and alkenylene moieties which can be partially substituted include ethylene, 1,2-propylene, 1,4-butylene, 1,5-pentylene, 1,6-hexamethylene, 1,7-heptamethylene, 1,8-octamethylene, 1,4-cyclohexylene, and mixtures thereof.

For the $R^1$ moieties, the degree of partial substitution with moieties other than 1,4-phenylene should be such that the soil release properties of the compound are not adversely affected to a significant degree. Generally, the degree of partial substitution which can be tolerated will depend upon the backbone length of the compound, with longer backbones generally having greater partial substitution for 1,4-pheneylene moieties. Usually, compounds where the $R^1$ comprise from about 50% to about 100% 1,4-phenylene moieties (from 0 to about 50% moieties other than 1,4-phenylene) have adequate soil release activity. For example, polyesters with a 40:60 mole ratio of isophthalic (1,3-phenylene) to terephthalic (1,4-phenylene) acid have adequate soil release activity. However, because most polyesters used in fiber making comprise ethylene terephthalate the $R^2$ moieties are 1,2-propylene moieties. The value for each n is at least about 6, and preferably is at least about 10.

The value for each n usually ranges from about 12 to about 113. Typically, the value for each n is in the range of from about 12 to about 43.

Cellulosic derivatives are also functional as soil release agents. Examples of such agents include but are not limited to hydroxyethers of cellulose such as Methocel® available from Dow Chemical; and certain cationic cellulose ether derivatives such as Polymer JU-125®, JR-400, and JR-30M® available from Union Carbide. Additional examples of cellulosic polymeric soil release agents include methyl cellulose, hydroxypropyl methylcellulose, hydroxybutyl methylcellulose, or mixtures thereof wherein said cellulosic polymer has a viscosity in a 2% aqueous solution at 20° C. of 15 to 75,000 centiposie. Other effective soil release agents are cationic guar gums such as Jaguar Plus® available from Stein Hall and Gendrive 458® available from General Mills. A more complete disclosure of highly preferred soil release agents is contained in European Patent Application No. 185,427 to Gosselink which was published Jun. 25, 1986, and U.S. Pat. No. 5,207,933 to Trinh et al. which issued May 4, 1993, both of which are incorporated herein by reference.

Bacteriocides

Examples of bacteriocides which can be employed in the compositions of the present invention include but are not limited to parabens such as methyl, glutaraldehyde, formaldehyde, 2-bromo-2-nitropropane- 1,3-diol sold by Inolex Chemicals under the trade name Bronopol®, and a mixture of 5-chloro-2-methyl-4-isothiazoline-3-one and 2-methyl-4-isothiazoline-3-one sold by Rohm and Hass Company under the trade name Kathon® CG/ICP. Typical levels of bacteriocides used in the present compositions are about 1 ppm to about 2,000 ppm by weight of the composition, depending on the type of bacteriocide selected. Methyl paraben is especially effective for mold growth in aqueous fabric softening compositions with under 10% by weight of the diester component.

Silicones

Dimethylpolysiloxane (silicone) or modified silicone can be added to the composition of this present invention, in order to enhance the softening property and water-absorbency of the unsaturated quaternary ammonium salt of formula (I)–(III).

Dimethypolysiloxane or a modified silicone, having a viscosity of 20–10000 cps at 25° C., is preferred.

Modified silicones useful in the present invention include, for example, polyoxethylene modified silicone and amino-modified silicone, wherein the amount of the modification is preferably less than 10%.

It is preferable that dimethylpolysiloxane or modified silicones are emulsified with a polyoxyethylene-type nonionic surfactant or a monoalkylcationic-type or dialkylcationic-type cationic surfactant prior to their use.

Other Optional Components

The present invention can include other optional components conventionally used in textile treatment compositions, for example, colorants, preservatives, optical brighteners, opacifiers, fabric conditioning agents, surfactants, stabilizers such as guar gum, anti-shrinkage agents, anti-wrinkle agents, fabric crisping agents, anti-spotting agents, fungicides, anti-corrosion agents, antifoam agents, and the like.

An optional additional softening agent of the present invention is a nonionic fabric softener material. Typically, such nonionic fabric softener materials have an HLB of from about 2 to about 9, more typically from about 3 to about 7. Such nonionic fabric softener materials tend to be readily dispersed either by themselves, or when combined with other materials such as single-long-chain aklkyl cationic surfactant, mixture with other materials as set forth hereinafter, use of hotter water, and/or more agitation. In general, the materials selected should be relatively crystalline, higher melting, (e.g., 50° C. or greater) and relatively water-insoluble.

The level of optional nonionic softener in the solid composition is typically from about 10% to about 40%, preferably from about 15% to about 30%, and the ratio of the optional nonionic softener to the ester quaternary (TEQ) of the present invention is from about 1:6 to about 1:2, preferably from about 1:4 to about 1:2. The level of optional nonionic softener in the liquid composition is typically from about 0.5% to about 10%, preferably from about 1% to about 5%. Preferred nonionic softeners are fatty acid partial esters of polyhydric alcohols, or anhydrides thereof, wherein the alcohol, or anhydride, contains from 2 to about 18, preferably from 2 to about 8, carbon atoms, and each fatt acid moiety contains from about 12 to about 30, preferably from about 16 to about 20, carbon atoms. Typically, such softener contain from about one to about 3, preferably about 2 fatty acid groups per molecule.

The polyhydric alcohol portion of the ester can be ethylene glycol, glycerol, poly (e.g., di-, tri-, tetra, penta-, and/or hexa-) glycerol, xylitol, sucrose, erythritol, pentaerythritol, sorbitol or sorbitan. Sorbitan esters and polyglycerol monostearate are particularly preferred. The fatty acid portion of the ester is normally derived from fatty acids having from about 12 to about 30, preferably from about 16 to about 20, carbon atoms, typical examples of said fatty acids being lauric acid, myristic acid, palmitic acid, stearic acid and behenic acid.

Highly preferred optional nonionic softening agents employable in the present invention include but are not limited to the sorbitan esters, which are esterified dehydration products of sorbitol, and the glycerol esters. Sorbitol, which is typically prepared by the catalytic hydrogenation of glucose, can be dehydrated in well known fashion to form mixtures of 1,4- and 1,5-sorbitol anhydrides and small amounts of isosorbides. An exemplary process is described in U.S. Pat. No. 2,322,821which is incorporated herein by reference. The foregoing types of complex mixtures of anhydrides of sorbitol are collectively referred to herein as "sorbitan". Further, one of ordinary skill in the art will recognize that this "sorbitan" mixture will also contain some free, uncyclized sorbitol.

Preferred sorbitan softening agents can be prepared by esterifying the "sorbitan" mixture with a fatty acyl group in standard fashion, e.g., by reaction with a fatty acid halide or fatty acid. The esterification reaction can occur at any of the available hydroxyl groups, and various mono-, di-, etc., esters can be prepared. Mixtures of mono-, di-, tri-, etc., esters almost always result from such reactions, and the stoichiometric ratios of the reactants can be simply adjusted to favor the desired reaction product.

For commercial production of the sorbitan ester materials, etherification and esterification are generally accomplished in the same processing step by reacting sorbitol directly with fatty acids. Such a method is described more fully in MacDonald; "Emulsifiers:" Processing and Quality Control:, *Journal of the American Oil Chemists' Society*, Vol.45, October 1968. Details, including formulas of the preferred sorbitan esters, can be found in U.S. Pat. No. 4,128,484, which is incorporated herein by reference. Certain derivatives of the preferred sorbitan esters herein, especially the "lower" ethoxylates thereof (i.e., mono-, di-, and trimesters) wherein one or more of the unesterified -OH groups contain one to about twenty oxyethylene moieties [Tweens®] are also useful in the composition of the present invention. Therefore, for purposes of the present invention, the term "sorbitan ester" includes such derivatives.

For the purposes of the present invention, it is preferred that if sorbitan esters are employed, that a significant amount of di- and tri- sorbitan esters are present in the ester mixture. Ester mixtures having from 20–50% di-ester and 10–35% of tri- and tetra-esters are preferred. Commercially available material, such as sorbitan mono-ester (e.g., monostearate), contains significant amounts of di- and tri-esters and a typical analysis of sorbitan monostearate indicates that it comprises about 27% mono-, 32% di- and 30% tri- and tetra-esters. Commercial sorbitan monostearate therefore is a preferred material. Mixtures of sorbitan stearate and sorbitan palmitate having stearate/palmitate weight ratios varying between 10:1 and 1:10, and 1,5-sorbitan esters are useful. Both the 1,4- and 1,5-sorbitan esters are also useful herein.

Other useful alkyl sorbitan esters for use in the softening compositions herein include sorbitan monolaurate, sorbitan monimyristate, sorbitan monopalmitate, sorbitan monobehenate, sorbitan monooleate, sorbitan dilaurate, sorbitan dimyristate, sorbitan dipalmitate, sorbitan distearate, sorbittan dibehenate, sorbitan dioleate, and mixtures thereof, and mixed tallowalkyl sorbitan mono- and di-esters. Such mixtures are readily prepared by reacting the foregoing hydroxy-substituted sorbitans, particularly the 1,4- and 1,5-sorbitans, with the corresponding acid or acid chloride in a simple esterification reaction. It is to be recognized, of course, that commercial materials prepared in this manner will comprise mixtures usually containing minor proportions of uncyclized sorbitol, fatty acids, polymers, isosorbide structures, and the like. In the present invention, it is preferred that such impurities are present at as low a level as possible.

The preferred sorbitan esters can contain up to about 15% by weight of esters of the $C_{20}$–$C_{26}$ and higher, fatty acids, as well as minor amounts of $C_8$, and lower, fatty esters. Glycerol and polyglycerol esters, especially glycerol, diglycerol, triglycerol, and polyglycerol mono- and/or di-esters, preferably mono-, are preferred herein. Glycerol esters can be prepared from naturally occurring triglyrides by normal extraction, purification and/or interesterification processes or by esterification processes of the type set forth hereinbefore for sorbitan esters. Partial esters of glycerin can also be ethoxylated to form usable derivatives that are included within the term "glycerol esters."

Useful glycerol and polyglycerol esters include mono-esters with stearic, oleic, palmitic, lauric, isostearic, myristic, and/or behenic acids and the diesters of stearic, ileic, palmitic, lauric, isostearic, behenic, and/or myristic acids. Typical mono-ester contains some di- and tri-ester, etc.

The "glycerol esters" also include the polyglycerol, e.g., diglycerol through oxtaglycerol esters. The polyglycerol polyols are formed by condensing glycerin or epichlorohydrin together to link the glycerol moieties via ether linkages. The mono- and/or diesters of the polyglycerol polyols are preferred, the fatty acyl groups typically being those described hereinbefore for the sorbitan and glycerol esters.

The present invention will now be illustrated by the following nonlimiting examples.

EXAMPLE 1
PROCESS FOR PREPARING 90% ACTIVE SOFTENING COMPOSITION

| Balance of materials - TEEA | | |
|---|---|---|
| BHT | = | 1.42 g |
| Hypophosphorous acid (50% solution) | = | 1.24 g |
| Distilled Tallow or $C_{16}$–$C_{18}$ with $C_{18}$ Unsaturates Fatty Acid | = | 710 g |
| Triethanolamine (TEA) | = | 231.8 g |

TEEA (a fatty acid ester amine of TEA) was prepared in a 2L-resin kettle connected to an overhead stirrer, three-ball Snyder column, addition funnel, distillation setup, nitrogen sparge and temperature control. The system was vacuum-leak tested before starting the experiment.

Molten fatty acid, antioxidants and hypophosphorous acid were charged to the reaction flask and kept at 65–75° C. under nitrogen. The reaction apparatus was then purged by pulling vacuum to 29" Hg and breaking vacuum with nitrogen three times in order to remove any air in the system. TEA was then added and after addition, the reaction mixture was heated up with a ramp rate of 1.75° C. per minute. As the reaction temperature reached 105° C., vacuum was pulled to 26" Hg and the reaction was continued heating up to 195–200° C. At this temperature and pressure, the reaction was held for approximately 20 minutes. Free fatty acid was approximately 0.07 meq/g. Moisture level should be <0.1% or drying may be required prior to quaternization.

| Balance of materials - Ester quat (TEQ) of the present invention | | |
|---|---|---|
| TEEA | = | 306.3 g |
| Isopropanol | = | 41.3 g |
| DMS | = | 62.1 g |
| EDTA (40% solution) | = | 0.26 g |
| BHT | = | 0.21 g |

TEEA was charged into the reactor and heated to 80° C. under nitrogen, and dried for approximately 30 minutes. The dried TEEA was then cooled to 60° C. after which the isopropanol was added (5% batch weight). The heat mantle was then removed and the DMS was added dropwise over a time period of about 20 minutes. The reaction temperature increased from about 50° C. to 85° C. because of the exotherm. The contents of the reactor were then allowed to digest at 85–90° C. for approximately two hours. EDTA and BHT were then added, and the remaining isopropanol (5%) was added to the mixture.

The resultant product had the following characteristics:

| | |
|---|---|
| Appearance: | viscous liquid at room temperature |
| Solvent: | isopropanol (IPA) |
| Activity: | 90% active |
| Color (Gardener scale): | 2 |
| pH (1% in 50/50 IPA:water) | 3–4 |
| Specific Gravity: | 0.978 g/cc |
| Cloud Point: | 38–39° C. |
| Pour Point: | 19–21° C. |
| Water: | 0.5% or less |

EXAMPLE 2
"STANDARD" RINSE CYCLE SOFTENER FORMULATION (7.5% Active)

| Raw Materials: | |
|---|---|
| Quaternary salt of the present invention | 8.40% |
| DI-water | 91.60% |
| 1 N HCl | pH 2.7–3.2 |
| Fragrance | q.s. |
| Dye/colorant | q.s. |
| Anti-microbial | q.s. |

Preheat water to between 45 and 60° C. Add the heated water to a suitable vessel and acidify to a pH of 2.7–3.2 with 1 N HCl. Add the warmed quaternary salt to the acidified water while agitating and maintaining a temperature of 45–60° C. Cool the dispersion while agitating. Solubilize fragrance into the softener dispersion at 40° C. Add dye and preservative as desired. Adjust weight with DI-water. Dispersion is storage stable within a temperature range of 4 to 50° C.

EXAMPLE 3
"Ultra" RINSE CYCLE SOFTENER FORMULATION (24% Active)

| Raw Materials: | |
|---|---|
| Quaternary salt of the present invention | 26.80% |
| DI-water | 73.20% |
| 1 N HCl | pH 2.7–3.2 |
| 10% aqueous Calcium Chloride ($CaCl_2$) solution | |
| Fragrance | q.s. |
| Dye/Colorant | q.s. |
| Anti-microbial | q.s. |

Preheat DI-water to 50–60° C. Charge DI-water to mixing vessel and acidify water to a pH of 2.7–3.2 with 1 N HCl.

Add the warmed quaternary salt to the acidified water with agitation while maintaining a temperature of 50–60° C. After addition of 73% of active, add $CaCl_2$ solution to the stirring dispersion. Make a second salt addition after 84% of active is added, and a third minor salt addition at completion of actives addition. Continue agitation to insure a smooth, homogeneous dispersion. Cool to 40° C. with agitation. Solublize fragrance into the softener dispersion. Adjust viscosity to the desired level with addition of $CaCl_2$ solution. Add color and preservative. Adjust weight with DI-water. Dispersion is storage stable within a temperature range of 4–50° C. For an even higher level of softening, dispersions containing 28–40% actives can be easily formulated employing techniques similar to those shown above.

EXAMPLE 4

ULTRA RINSE CYCLE SOFTENER FORMULATION (28% Active)

| Raw Materials: | |
|---|---|
| Quaternary salt of the present invention | 156 g |
| DI-water | 315 g |
| 1 N HCl | pH 2.7–3.2 |
| 10% aqueous Calcium Chloride ($CaCl_2$) solution | |
| Fragrance | q.s. |
| Dye/Colorant | q.s. |
| Anti-microbial | q.s. |

The DI-water is preheated to 50–60° C. and charged to the mixing vessel and acidified to a pH of 2.7–3.2 with 1N HCl. The molten quaternary salt is then slowly added to the mixing vessel with mixing while the temperature is maintained at about 60° C. The mixture is then cooled to 40° C. with agitation wherein the fragrance solubilized into the softener dispersion. The viscosity is then adjusted to the desired level with addition of $CaCl_2$ solution, and color and preservatives added. Lastly, the weight is adjusted with DI-water. The dispersion is storage stable within a temperature range of 4–50° C.

We claim:

1. A textile softening composition with improved stability and softening performance which comprises a fabric softening effective amount of a quaternary ammonium salt having mono-, di-, and tri-ester components of the following formulae (I)–(III):

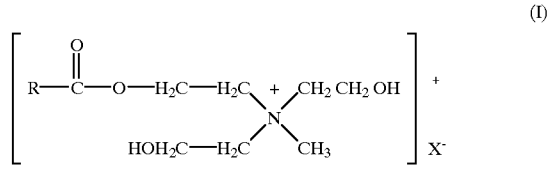

(I)

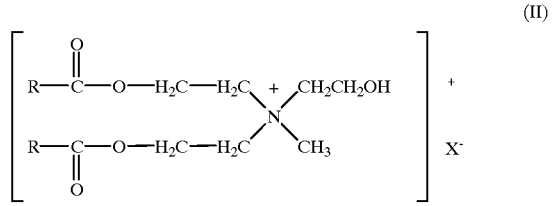

(II)

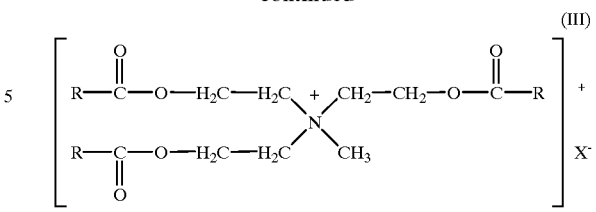

(III)

wherein each R can be the same or different and is represented by a substituted or unsubstituted hydrocarbon radical having from 12–22 carbon atoms and an Iodine Value of from about 20 to about 90, wherein said diester component (II) comprises greater than about 55 wt % and the triester component (III) comprises less than about 25 wt % based on the total amount of the quaternary ammonium salt and X⁻ presents a softener compatable anion.

2. The softener composition of claim 1 wherein the cis/trans isomer ratio of said quaternary ammonium salt is the range of from about 80/20 to 95/5.

3. The softener composition of claim 1 wherein the cis/trans ratio is less than 90/10.

4. The softener composition of claim 1 wherein said quaternary ammonium salt comprises 3–50% by weight based on the total weight of the composition.

5. The composition of claim 1 wherein said quaternary ammonium salt comprises greater than about 55 wt % diester component (II) and less than about 20 wt % triester (III) component.

6. The composition of claim 1 wherein said quaternary ammonium salt comprises greater than about 60 wt % diester component (II) and less than about 15 wt % triester (III) component.

7. The composition of claim 1 wherein said R groups represent a hydrocarbon radical having from 16 to 22 carbon atoms and an Iodine value from about 30 to about 60.

8. The composition of claim 1 wherein said R groups represent a hydrocarbon radical having from 16 to 22 carbon atoms and an Iodine value from about 45 to about 55.

9. A method for softening textiles which comprises applying thereto a softening effective amount of the composition of claim 1.

10. A method for the softening, conditioning and/or lubricating hair or skin which comprises applying to said hair or skin a softening, conditioning and lubricating effective amount of the quaternary ammonium salt of claim 1.

11. A process for the preparation of a quaternary ammonium salt which comprises reacting, at a temperature of from about 170° C. to 210° C.:

I) a $C_{12}$–$C_{22}$ substituted or unsubstituted fatty acid or mixture of fatty acids having an Iodine Value of from about 20 to about 90, and having less than about 20% trans double bonds, with II) an alkanolamine of the formula:

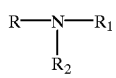

wherein R, $R_1$ and $R_2$ are independently selected from $C_2$–$C_4$ hydroxyalkyl groups, wherein the molar ratio of said fatty acid to alkanol amine is from about 1.6–1.8, and wherein said reaction temperature is increased from about 70° C. to a range of from about 170° to 210° C., wherein the rate of temperature increase is maintained within a range of from about 0.8° C. to 3° C. per minute in order to obtain an ester composition with greater than about 55 wt % diester component and less than about 25 wt % triester component, and quaternizing same in order to obtain to quaternary ammonium salt.

12. The process of claim 11 wherein the temperature of the reaction is increased at a rate of 1.25°–3° C. per minute from a starting temperature of 70° C. up a temperature of from about 170° C. to 210° C.

13. The process of claim 11 wherein said fatty acid is a substituted or unsubstituted $C_{16}$–$C_{22}$ fatty acid having an Iodine value of from about 30 to 60.

14. The process of claim 11 wherein said fatty acid is a substituted or unsubstituted $C_{16}$–$C_{22}$ fatty acid having an Iodine value of from about 45 to 55.

15. The process of claim 11 wherein said fatty acid is derived from tallow, soy, palm, palm kernal, rape seed, lard or mixtures thereof.

16. The process of claim 11 wherein said fatty acid is derived from partially hydrogenated tallow, soy, palm, palm kernal, rape seed, lard or mixtures thereof.

17. The process of claim 11 wherein said alkanolamine is selected from the group consisting of triethanolamine, propanol diethanolamine, ethanol diisopropanolamine, triisopropanol amine and mixtures thereof.

18. The process of claim 11 wherein the molar ratio of fatty acid to alkanol amine is about 1.7.

19. The process of claim 11 wherein said fatty acid has less than about 10% trans isomer.

20. The process of claim 11 wherein the alkylating agent is selected from the group consisting of methyl chloride, benzyl chloride, diethyl sulfate, dimethyl carbonate, trimethyl phosphate, dimethyl sulfate or mixtures thereof.

21. The process of claim 11 wherein a solvent is not employed.

22. The process of claim 11 wherein a solvent is employed.

23. The process of claim 22 wherein said solvent is selected from the group consisting of $C_1$–$C_6$ alcohols, glycol, fatty acid, mono-, di-, or tri-glycerides, and mixtures thereof.

* * * * *